United States Patent
Ouyang (10) Patent No.: US 12,265,053 B2
(45) Date of Patent: Apr. 1, 2025

(54) APPARATUS, METHOD AND SENSOR FOR MEASURING GAS CONCENTRATION

(71) Applicant: SHENZHEN CAMBRI ENVRIONMENTAL TECHNOLOGY CO., LTD., Shenzhen (CN)

(72) Inventor: Bin Ouyang, Zhongshan (CN)

(73) Assignee: SHENZHEN CAMBRI ENVIRONMENTAL TECHNOLOGY CO., LTD., Shenzhen (CN)

(*) Notice: Subject to any disclaimer, the term of this patent is extended or adjusted under 35 U.S.C. 154(b) by 500 days.

(21) Appl. No.: 17/577,913

(22) Filed: Jan. 18, 2022

(65) Prior Publication Data
US 2022/0136994 A1 May 5, 2022

Related U.S. Application Data

(63) Continuation of application No. PCT/CN2020/085702, filed on Apr. 20, 2020.

(30) Foreign Application Priority Data

Apr. 13, 2020 (CN) .......................... 202010283231.3

(51) Int. Cl.
 G01N 27/407 (2006.01)
 G01N 27/27 (2006.01)
(52) U.S. Cl.
 CPC .......... *G01N 27/407* (2013.01); *G01N 27/27* (2013.01)
(58) Field of Classification Search
 CPC .. G01N 27/407; G01N 27/27; G01N 27/4035; G01N 33/0039; G01N 33/004;
 (Continued)

(56) References Cited

U.S. PATENT DOCUMENTS 5,716,506 A * 2/1998 Maclay ............... G01N 27/404
 204/426
5,719,325 A * 2/1998 Kiesele ............... G01N 27/404
 73/23.31
(Continued)

FOREIGN PATENT DOCUMENTS

CN 1790001 6/2006
CN 201653961 11/2010
(Continued)

OTHER PUBLICATIONS

Metz et al, "Transport of water vapor and inert gas mixtures through highly selective and highly permeable polymer membranes" (Year: 2004).*
(Continued)

*Primary Examiner* — Eyob Hagos
(74) *Attorney, Agent, or Firm* — Grossman, Tucker, Perreault & Pfleger, PLLC (57) ABSTRACT

An apparatus, method and sensor for measuring gas concentration. The apparatus includes a sensing unit and a processing unit. The sensing unit includes a first selective water vapour-permeable membrane, a first working electrode and a second working electrode. The first selective water vapour-permeable membrane allows the first working electrode to be in contact with water molecules while to prevent this first working electrode from being in contact with the gas molecules to be measured. The first working electrode generates an electrical signal caused by change in relative humidity, the second working electrode generates a superimposed electrical signal caused by the change in relative humidity and the gas molecules to be measured, and the processing unit acquires concentration of the gas based on the electrical signal and the superimposed electrical signal.

10 Claims, 5 Drawing Sheets

(58) Field of Classification Search
CPC .......... G01N 33/0042; G01N 33/0037; G01N 27/333
See application file for complete search history.

(56) References Cited

U.S. PATENT DOCUMENTS

| | | | | |
|---|---|---|---|---|
| 6,488,836 | B1* | 12/2002 | Nakata | G01N 27/4074 204/426 |
| 6,896,781 | B1* | 5/2005 | Shen | G01N 27/4175 204/426 |
| 7,887,683 | B2* | 2/2011 | Dalmia | G01N 27/4071 204/426 |
| 8,920,627 | B2* | 12/2014 | Fleischer | G01N 27/414 257/253 |
| 9,029,045 | B2* | 5/2015 | Satou | H01M 8/0245 429/535 |
| 10,031,097 | B1 | 7/2018 | Han et al. | |
| 2012/0260732 | A1* | 10/2012 | Humbert | G01N 27/223 216/13 |
| 2014/0138259 | A1 | 5/2014 | Mickelson et al. | |
| 2016/0069850 | A1* | 3/2016 | van der Avoort | G01N 29/4436 73/24.01 |
| 2017/0350846 | A1* | 12/2017 | Cook | G01N 31/222 |
| 2019/0079039 | A1 | 3/2019 | Li et al. | |
| 2019/0250117 | A1* | 8/2019 | Itoh | G01N 27/22 |
| 2020/0083541 | A1* | 3/2020 | Swiegers | H01M 8/0239 |

FOREIGN PATENT DOCUMENTS

| | | | | |
|---|---|---|---|---|
| CN | 102095788 | | 6/2011 | |
| CN | 102146648 | | 8/2011 | |
| CN | 102472717 | | 5/2012 | |
| CN | 104610018 | | 5/2015 | |
| CN | 106248752 | | 12/2016 | |
| CN | 106770523 | | 5/2017 | |
| CN | 107478692 | | 12/2017 | |
| CN | 208026697 | | 10/2018 | |
| CN | 109060899 | | 12/2018 | |
| CN | 109341735 | | 2/2019 | |
| CN | 110596327 | | 12/2019 | |
| CN | 110672613 | | 1/2020 | |
| CN | 110823958 | | 2/2020 | |
| CN | 111487304 | A | 8/2020 | |
| DE | 102016115004 | | 2/2018 | |
| EP | 3191830 | B1* | 10/2018 | ........... G01L 9/0016 |
| JP | 2008275557 | A | 11/2008 | |
| WO | WO-2015158599 | A1* | 10/2015 | ............ G01L 23/10 |

OTHER PUBLICATIONS

Pang et al, "The impacts of water vapour and co-pollutants on the performance of electrochemical gas sensors used for air quality monitoring" (Year: 2018).*

International Search Report from corresponding PCT Appln. No. PCT/EP2020/085702, dated Jan. 13, 2021.

First Office Action from related Chinese Appln. No. 202010283231. 3, mailed Nov. 27, 2020. English translation attached.

Second Office Action from related Chinese Appln. No. 202010283231. 3, mailed May 6, 2021. English translation attached.

Communication pursuant to Article 94(3) EPC of EP Corresponding Application 20931051.5 issued on Sep. 27, 2023 from the EPO. (8 Pages).

First Office Action of CN Corresponding Application 202111134421.X issued on Jan. 30, 2024 from the CNIPA. (English Translation Attached).

Second Notice of Office Action from priority application Cn 202111134421.X issued on Aug. 5, 2024. (5 pages) english translation attached.

* cited by examiner

APPARATUS, METHOD AND SENSOR FOR MEASURING GAS CONCENTRATION

CROSS-REFERENCE TO RELATED APPLICATIONS

The present application is a continuation of International Application No. PCT/CN2020/085702, filed on Apr. 20, 2020, which claims priority to Chinese Patent Application No. 202010283231.3, filed on Apr. 13, 2020, both of which are hereby incorporated by reference in their entireties.

FIELD

The present disclosure relates to the technical field of atmospheric monitoring, and more particularly, to an apparatus for measuring gas concentration, a method for measuring gas concentration and a sensor for measuring gas concentration.

BACKGROUND

In the fields of air pollution control such as locating pollution sources, monitoring pollutant emission characteristics, improving air quality and studying population health effects related to exposure to atmospheric pollutants, it is getting increasingly important to accurately measure the concentrations of atmospheric pollutants and accurately construct distribution maps of these pollutants at ultrahigh temporal and spatial resolutions.

In order to achieve the above goals, miniaturized gas sensors shall be used, such as metal-oxide semiconductor gas sensors or electrochemical gas sensors. However, the miniaturized gas sensors such as the electrochemical sensors are usually configured for measuring air pollutants on the ppm (part per million) level, mainly for safety production pre-warning. However, in the outdoor environment, air pollutants such as carbon monoxide (CO), nitrogen monoxide (NO), nitrogen dioxide ($NO_2$), ozone ($O_3$) and sulfur dioxide ($SO_2$) are usually present at levels below 1 ppm, and among these, some gases such as $NO_2$ and $O_3$ may commonly have a concentration from several ppb (parts per billion) to a few tens of ppbs, usually no more than 200 ppbs. As such, conventional miniaturized gas sensors generally do not provide enough sensitivity for measuring concentrations of air pollutants in outdoor environment.

In the recent years, by increasing the surface area of electrodes and decreasing the electronic noise of circuits, electrochemical sensors have gradually achieved a sensitivity on the ppb level. However, changes in ambient temperature and relative humidity may bring changes in voltage readings of an electrode of the electrochemical sensor, which, when superimposed on the target electrical signal generated by electrochemical redox reactions of gases on the surfaces of the electrodes, affect the gas measurement. When the concentration of the gas to be measured is on the ppb level, the signal generated by the electrochemical reaction of gases is very weak, and a baseline change which is caused by change in temperature and relative humidity in the environment where the sensor is located cannot be ignored and must therefore be corrected for. Correction methods proposed to-date for the temperature and relative humidity induced baseline signal changes of the sensor mainly include uni- or multi-variate linear regression, machine learning, artificial neural network or high dimensional model characterization, but these methods suffer from many disadvantages such as black-box operation, failure to reflect real physical laws, complexity in algorithm, large deviation in measurement result of concentrations which altogether limit their applicability in the real world.

SUMMARY

The present disclosure aims to solve at least one of the above-mentioned technical problems in the related art. To this end, the first objective of the present disclosure is to provide an apparatus for measuring gas concentration, which can accurately retrieve gas concentrations by quickly and effectively correcting for the ambient temperature and relative humidity induced interference signals of the gas sensors.

The second objective of the present disclosure is to provide a sensor for measuring gas concentration.

The third objective of the present disclosure is to provide a method for measuring gas concentration.

In order to achieve the above objectives, an embodiment in a first aspect of the present disclosure provides an apparatus for measuring gas concentration, including a sensing unit and a processing unit. The sensing unit may include a first selective water vapour-permeable membrane, a first working electrode and a second working electrode. The first selective water vapour-permeable membrane may be configured to allow the first working electrode to be in contact with ambient water molecules but not with gas molecules to be measured. The first working electrode may be configured to generate an electrical signal caused by change in ambient relative humidity, the second working electrode may be configured to generate a superimposed electrical signal caused by both the change in ambient relative humidity and reaction of the gas molecules to be measured, and the processing unit may be configured to acquire the concentration of the gas to be measured based on the electrical signal caused by the change in ambient relative humidity and the superimposed electrical signal.

The apparatus for measuring gas concentration according to the embodiment of the present disclosure provides a new way of measuring gas concentration, by providing the first selective water vapour-permeable membrane, the first working electrode and the second working electrode. Specifically, the first working electrode mainly detects the electrical signal caused by change in ambient relative humidity, while the second working electrode detects the superimposed electrical signal caused by both change in ambient relative humidity and reaction of gas molecules to be measured on the electrode surfaces. This way, the first selective water vapour-permeable membrane isolates the electrical signal caused by changes in ambient relative humidity, and the processing unit acquires the electrical signal related to gas molecules to be measured by subtracting the temperature-related term, the relative humidity-related term and the baseline-related term from the superimposed electrical signal caused by both water molecules and gas molecules to be measured. Therefore, the apparatus can accurately determine the concentration of the gas to be measured by quickly and effectively correcting for the ambient temperature and relative humidity effects of the sensors used and has a wide applicability.

In some embodiments, the sensing unit may include a first sensor and a second sensor. The first sensor may include a first working electrode. The second sensor may include a second working electrode. The first working electrode may be in contact with an external environment through a sensing surface of the first sensor. The second working electrode may be in contact with the external environment through the sensing surface of the second sensor.

The first selective water vapour-permeable membrane may be applied on the sensing surface of the first sensor and covers the entire sensing surface. Alternatively, the first selective water vapour-permeable membrane may be provided on the surface of the first working electrode to allow the first working electrode to be in contact with ambient water molecules and prevent the first working electrode from being contact with gas molecules to be measured.

Alternatively, the sensing unit may include only one sensor including both the first working electrode and the second working electrode. The first working electrode and the second working electrode may be in contact with the external environment through the sensing surface of the sensor. Here, the first selective water vapour-permeable membrane may be applied on the surface of the first working electrode, or the first selective water vapour-permeable membrane may be provided on the sensing surface of the sensor and completely covers a part of the sensing surface through which the first sensing electrode is in contact with the external environment. In this way, the first working electrode is allowed to be in contact with ambient water molecules but is not in contact with gas molecules to be measured.

In some embodiments, the first selective water vapour-permeable membrane may be provided on the sensing surface of the one sensor and is configured to selectively cover the part of the sensing surface through which the second working electrode is in contact with the external environment. Alternatively, the sensing unit may further include a second selective water vapour-permeable membrane, the second selective vapour-permeable membrane is detachably or movably provided on the part of the sensing surface through which the second working electrode of the one sensor is in contact with the external environment, so as to selectively cover this part of the sensing surface. Alternatively, the sensing unit may further include a second selective water vapour-permeable membrane which is detachably or movably provided on the part of the sensing surface of a second sensor which is in contact with the external environment, so as to selectively cover the sensing surface. Alternatively, the sensing unit may further include a second selective water-permeable film which is detachably or movably provided on the surface of the second sensing electrode to selectively cover the surface.

In some embodiments, each sensor may further include at least one auxiliary electrode.

In some embodiments, the processing unit may acquire the concentration of the gas to be measured based on the following equation $$[P](t) = \frac{(W_2(t) - b \times A_2(t) - c)}{s};$$

or the first sensor may include a first auxiliary electrode, the second sensor may include a second auxiliary electrode, and the processing unit may acquire the concentration of the gas to be measured based on the following equation:

$$[P](t) = \frac{(W_2(t) - \alpha \times W_1(t) - b \times (A_2(t) - A_1(t)) - c)}{s},$$

where [P](t) represents the concentration of the gas to be measured, $W_2(t)$ represents a detected signal of the second working electrode, $W_1(t)$ represents a detected signal of the second auxiliary electrode, $A_2(t)$ represents a detected signal of the first working electrode, $A_1(t)$ represents a detected signal of the first auxiliary electrode, and a, b, c and s represent the empirical coefficient to be calibrated.

In order to achieve the above objectives, an embodiment of the present disclosure provides a sensor for measuring gas concentration, including:

a sensor body;

a first working electrode and a first selective water vapour-permeable membrane, the first working electrode being incorporated inside the sensor body and in contact with an external environment through a sensing surface.

Here, the first selective water vapour-permeable membrane may be provided on the sensing surface of the first working electrode which is in contact with the external environment, and completely covers the part of the sensing surface through which the first working electrode is in contact with the external environment, to allow the first working electrode to be in contact with ambient water vapour molecules and prevent it from being in contact with the gas molecules to be measured, so as to generate an electrical signal that is caused by the change in ambient relative humidity but is free of gas reaction signals. Alternatively, the first selective water vapour-permeable membrane may be provided on the surface of the first working electrode to allow it to be in contact with water vapour molecules in the ambient air and prevent it from being in contact with the gas molecules to be measured, so as to generate an electrical signal that is caused by the change in ambient relative humidity but is free of gas reaction signals.

The sensor for measuring gas concentration according to the embodiment of the present disclosure may, by providing the first selective water vapour-permeable membrane, allow the first working electrode to be in contact with only water molecules to generate a humidity electrical signal, and make this electrical signal caused by the change in ambient relative humidity be isolated so as to provide data support for calculating the concentration of the target gas.

In some embodiments, the sensor may further include a second working electrode within the sensor body, and the second working electrode is in contact with the external environment through the sensing surface.

In some embodiments, the first selective water-permeable film may be provided on the sensing surface and is configured to selectively cover or not cover a part of the sensing surface through which the second sensing electrode is in communication with the external environment; or the sensor may further include a second selective water vapour-permeable membrane, which is detachably or movably provided on the sensing surface through which the second working electrode is in contact with the external environment, to selectively cover the sensing surface; or the sensor may further include a second selective water vapour-permeable membrane detachably or movably provided on the surface of the second working electrode.

In order to achieve the above objects, an embodiment of the present disclosure discloses a method for measuring gas concentration, which can be applied to the above-mentioned apparatus for measuring gas concentration. The method includes acquiring an electrical signal caused by change in ambient relative humidity and a superimposed electrical signal caused by both the change in ambient relative humidity and by reaction of the target gas molecules on sensor electrode, and acquiring the concentration of the gas to be measured based on the electrical signal and the superimposed electrical signal.

With the method for measuring gas concentration according to embodiments of the present disclosure, based on the selective water vapour-permeable membrane, the first working electrode and the second working electrode, the electrical signal caused by change in ambient relative humidity can be isolated, and the electrical signal related to gas molecules to be measured can then be obtained by subtracting both the temperature-related and the relative humidity-related terms from the superimposed signal caused by both water molecules and gas molecules to be measured. The method can quickly and effectively correct for ambient temperature and relative humidity effects and accurately determine concentration of the gas to be measured, and therefore has a wide range of applicability.

In some embodiments, the concentration of the gas to be measured may be acquired based on the following equation $$[P](t) = \frac{(W_2(t) - b \times A_2(t) - c)}{s};$$

or the concentration of the gas to be measured may be acquired based on the following equation $$[P](t) = \frac{(W_2(t) - \alpha \times W_1(t) - b \times (A_2(t) - A_1(t)) - c)}{s},$$

where [P](t) represents the concentration of the gas to be measured, $W_2(t)$ represents a detected signal of the second working electrode, $W_1(t)$ represents a detected signal of the second auxiliary electrode, $A_2(t)$ represents a detected signal of the first working electrode, $A_1(t)$ represents a detected signal of the first auxiliary electrode, and a, b, c and s represent empirical coefficients to be calibrated.

Additional aspects and advantages of the present disclosure will be given partially in the following description, or partially become apparent from the following description, or can be learned from practicing of the present disclosure.

BRIEF DESCRIPTION OF DRAWINGS

The above and/or additional aspects and advantages of the present disclosure will become more apparent and more understandable from the following description of embodiments taken in conjunction with the accompanying drawings, in which.

DETAILED DESCRIPTION

The embodiments of the present disclosure will be described in detail below with reference to examples thereof as illustrated in the accompanying drawings, throughout which the same or similar elements, or elements having the same or similar functions, are denoted by the same or similar reference numerals. The embodiments described below with reference to the drawings are illustrative only, and are intended to explain, rather than limiting, the present disclosure.

In related art, a method for measuring gas concentration is performed by an optimization process based on a functional correlation between change in baseline signal from the electrochemical sensor and ambient temperature and relative humidity. Its algorithm is quite complicated and behaves more like a black box in which a user can hardly participate in the optimization process, and it cannot give a proper explanation for baseline drift caused by changes in temperature and relative humidity from a view of real physical laws, and the derived parameterized solution does not carry any physical implications. Further, this kind of method is just an algorithm model which is built and trained using measured data from a previous period of time, and thus it is a "localized" process and cannot be widely applied into a new measurement environment. Besides, since there may be various combinations of changes in temperature and relative humidity in the natural environment, it is often difficult to almost perfectly calculate the baseline drift signal of the electrochemical sensors caused by changes in temperature and relative humidity in the various environments through a parameterized equation, and thus will generate inaccurate measurement results.

In order to address the above-mentioned problems in the prior art, the embodiments of the present disclosure provide an apparatus and method that can accurately measure concentration of a target gas in ambient environments by accurately measuring the baseline drift signal from the gas sensor caused by changes in temperature and relative humidity and then removing such drift from the measured sensor signal.

An apparatus for measuring gas concentration according to an embodiment of the present disclosure will be described below with reference to FIG. 1.

Figure 1:
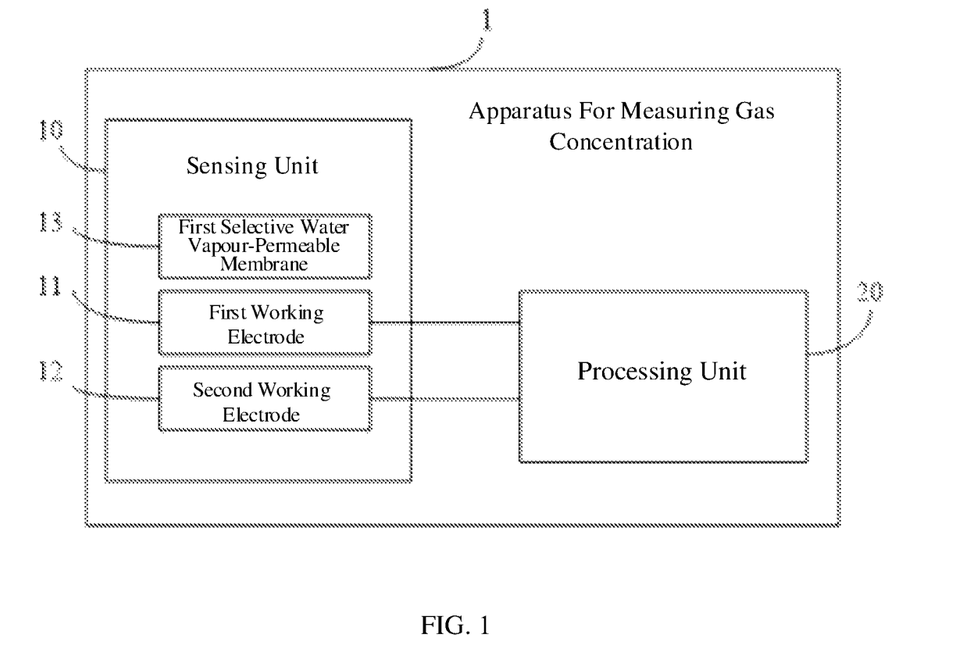
FIG. 1 is a block diagram of an apparatus for measuring gas concentration according to an embodiment of the present disclosure.

FIG. 1 illustrates an apparatus for measuring gas concentration according to an embodiment of the present disclosure. As shown in FIG. 1, an apparatus 1 according to the embodiment of the present disclosure includes a sensing unit 10 and a processing unit 20.

The sensing unit 10 includes at least a first working electrode 11, a second working electrode 12 and a first selective water vapour-permeable membrane 13. The first selective water vapour-permeable membrane 13 is configured to allow the first working electrode 11 to be in contact with water molecules and prevent the first working electrode 11 from being in contact with gas molecules to be measured. The first working electrode 11 is configured to generate an electrical signal caused by the change in ambient relative humidity. The second working electrode 12 is configured to be in contact with both gas molecules to be measured and water molecules, so as to generate a superimposed electrical signal caused by both change in ambient relative humidity and reaction of gas molecules to be measured on the second working electrode.

The processing unit 20 is electrically connected to the sensing unit 10. The processing unit 20 is configured to acquire detected signals from the first working electrode 11 and the second working electrode 12, and calculate the concentration of the gas to be measured using the electrical signal caused by change in ambient relative humidity as output by the first working electrode 11 and the superimposed electrical signal caused by both change in ambient relative humidity and gas molecules to be measured as generated from the second working electrode 12.

Particularly, the sensing unit 10 according to the embodiment of the present disclosure may include an electrochemical gas sensor, a semiconductor sensor or other chemical or physical sensors which can sense changes in temperature and relative humidity in the ambient environment, but is not limited to any of these examples. The apparatus 1 for measuring gas concentration according to the embodiment of the present disclosure provides a novel way of measuring gas concentrations by utilizing the first selective water vapour-permeable membrane 13, the first working electrode 11 and the second working electrode 12. Specifically, the first working electrode 11 mainly detects the relative humidity-related electrical signal caused by water molecules, the second working electrode 12 detects the superimposed electrical signal caused by both water molecules and gas molecules to be measured, while the presence of the first selective water vapour-permeable membrane 13 isolates the humidity electrical signal, and the processing unit 20 acquires the electrical signal related to gas molecules to be measured by subtracting a temperature related term, a humidity related term and a baseline related term from the superimposed electrical signal caused by both the water molecules and the gas molecules to be measured. Therefore, the apparatus accurately acquires the concentration of the gas to be measured by quickly and effectively correcting for the temperature and relative humidity in the ambient environment, and has a wide range of applicability.

Further, in an embodiment, in order to allow the first working electrode 11 to be in contact with water molecules but not the gas molecules to be measured, the first selective water vapour-permeable membrane 13 may be placed at a proper position in the sensing unit. Here, the first selective water vapour-permeable membrane 13 may be understood as a single-layer or multiple-layer membrane which only allows water molecules to permeate therethrough while substantially prevent gas molecules to be measured from permeating therethrough, that is, the first selective water vapour-permeable membrane has a selectively high permeability for water molecules over that for the gas molecules to be measured.

Figure 2:
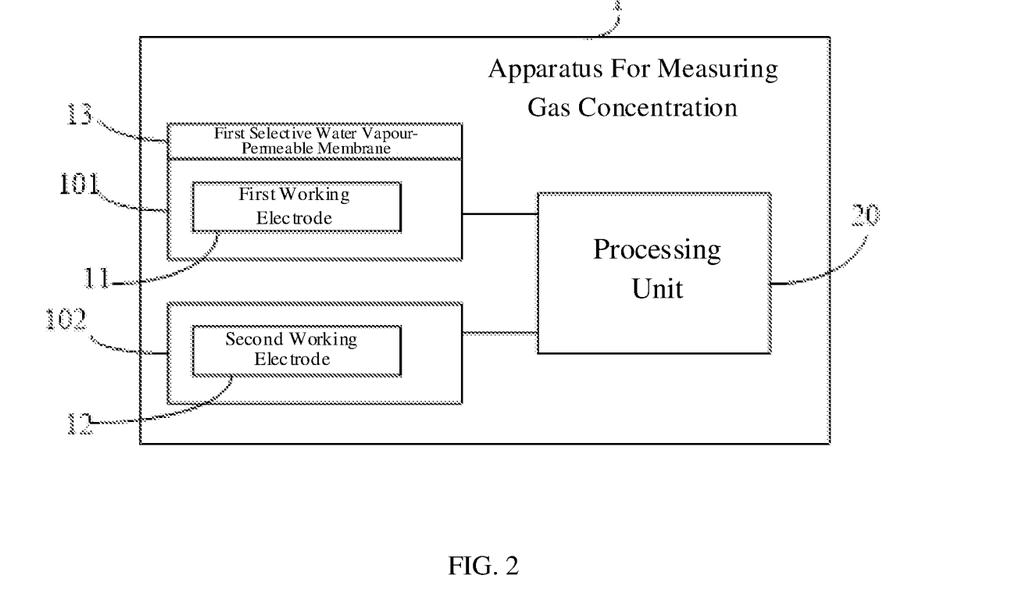
FIG. 2 is a block diagram of an apparatus for measuring gas concentration according to another embodiment of the present disclosure.

In some embodiments, as shown in FIG. 2, the sensing unit 10 includes two sensors, i.e., a first sensor 101 and a second sensor 102. The first sensor 10 includes a first working electrode 11. The first working electrode 11 is in contact with the external environment through a sensing surface of the first sensor 101. The first selective water vapour-permeable membrane 13 is provided on the sensing surface of the first sensor 101, for example, by adhering a selective water vapour-permeable membrane to the sensing surface. In this way, the first working electrode 11 within the first sensor 101 can only be in contact with water molecules, and is configured to generate the electrical signal caused by change in ambient relative humidity, transmit the electrical signal caused by change in ambient relative humidity to the processing unit 20, so as to provide data support for acquiring the concentration of the gas to be measured. Here, the sensing surface may be understood as a surface through which the gas molecules outside the sensor pass into the sensor.

Taking an electrochemical sensor as example, in order for the sensor to fully and properly function, four electrodes can be used including e.g., a working electrode, an auxiliary electrode, a counter electrode and a reference electrode. Here, the working electrode may be configured to oxidize or reduce a target gas, the counter electrode may be configured to balance a generated current, the reference electrode may be configured to fix the operation at a right potential, and the auxiliary electrode may be configured to compensate a zero current. There is no current flow between the reference electrode and the working electrode, so the working electrode can share the same potential with the reference electrode all the time.

Particularly, the sensing surface of the electrochemical sensor can be covered by a membrane which allows only water molecules to permeate therethrough. The gas molecules in the ambient air however cannot enter the sensor before permeating through the membrane. The membrane may have a thickness from several micrometers to several hundreds of micrometers provided that, in comparison with a sensor without this membrane arranged on the sensing surface, this membrane does not significantly slow down the diffusion speed of water molecules into the sensor and the diffusion speed of water molecules out of the sensor, but can fully prevent gas molecules to be measured from permeating into the sensor. To the above end, the membrane must satisfy the following condition, i.e., this membrane has a good diffusivity for water molecules that is sufficient for the first working electrode 11 to effectively sense change in relative humidity in the external environment so as to generate the electrical signal caused by change in ambient relative humidity due to the water molecules, but this membrane can have a very low diffusivity for the various gas molecules to be measured such that the first working electrode 11 does not respond to the target gas to be measured.

One such example of the selective water vapour-permeable membrane is the proton exchange polymer membrane that has been widely used in fuel cells. On the molecular level, these membranes typically contain a hydrophobic backbone and highly hydrophilic end group(s). Due to the presence of the latter, water molecules can bond strongly with the polymer and rapidly permeate through the membrane without significant energy barrier. To increase chemical resistance and field lifetime, all hydrogen atoms in the polymer membrane except the ones in the sulfonic end group are often substituted by fluorine atoms, and to increase the bonding strength between hydrogen bond donors and receptors, the hydrophilic end group is often chose as being sulfonic, and widely-known such perfluorosulfonic proton exchange membranes are, e.g. the Nafion membrane used to be manufactured by Dupont and now by Chemour, the Gore-Select membrane by Gore, and the Dongyue proton exchange membrane by Dongyue, the Dow membrane by Dow Chemical, the Aciplex membrane by Asahi Kasei Corporation and the Flemion membrane by Asahi Glass. On the other hand, many important atmospheric pollution gases, such as NO, $NO_2$, $SO_2$, CO and $O_3$, cannot effectively permeate through these membranes due to their very low diffusivities within the membranes, and therefore cannot reach the surface of the working electrode of the sensing unit and thus fail to generate an electrical signal. However, water molecules can quickly diffuse through the membrane and thus the electrical signal caused by change in relative humidity in external environment can be effectively recorded by the sensor.

The selective water vapour-permeable membrane according to the embodiments of the present disclosure is not limited to the above proton exchange membrane. Any membrane which can allow water molecules to permeate therethrough efficiently but has low permeability through the target gas and thus prevents gas molecules from reaching the working electrode can be used for the above purpose. These include but are not limited to the sulfonated polyetheretherketon (SPEEK) membrane, the poly(ethylene oxide)-poly(butylene terephthalate) (PEO-PBT) membrane, the polydopamine membrane and the polyether block amide (PBA) membrane with trade names of PEBAX by Arkema and VESTAMID by Evonik Industries.

Further, since the first sensor 101 is provided with the first selective water vapour-permeable membrane 13 at the sensing surface, the first sensor 101 cannot be in contact with gas molecules to be measured and cannot measure the gas concentration. The second sensor 102 without the first selective water vapour-permeable membrane 13 can be in contact with both the gas molecules to be measured and water molecules in the air. The second sensor 102 includes a second working electrode 12 which is in contact with the external environment through a sensing surface of the second sensor 102. The second working electrode 12 detects an electrical signal which is a superimposed electrical signal caused by both the gas molecules to be measured and water molecules, and transmits the superimposed electrical signal to the processing unit 20 to provide data support for calculating the concentration of the gas to be measured.

Figure 3:
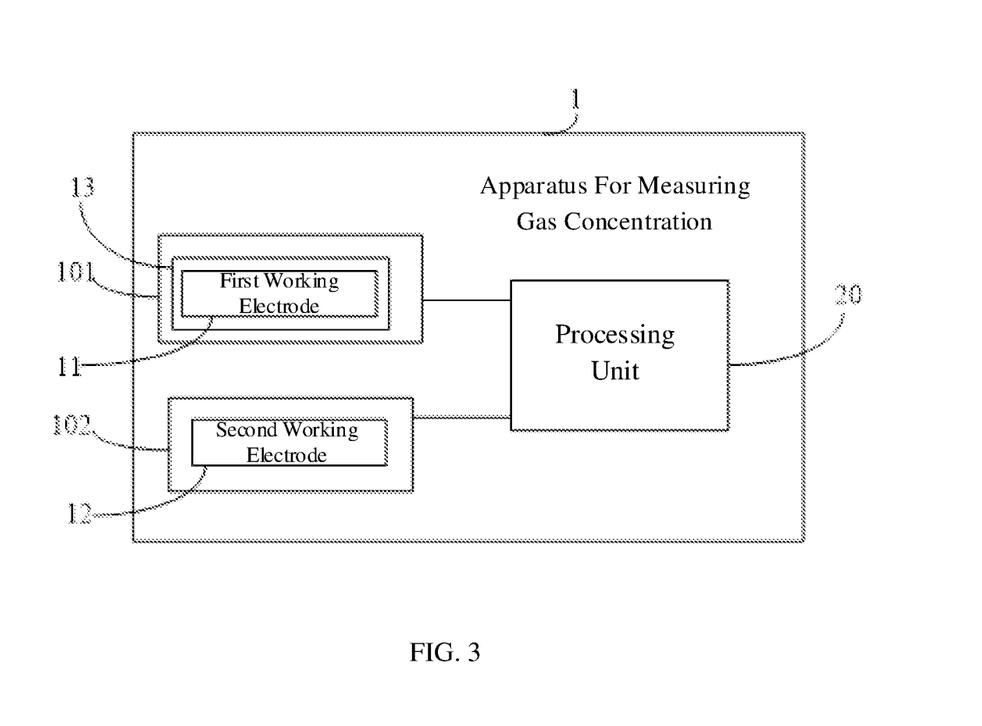
FIG. 3 is a block diagram of an apparatus for measuring gas concentration according to yet another embodiment of the present disclosure.

In some other embodiments, the surface of the working electrode inside the first sensor 101 may be covered by the first selective water vapour-permeable membrane 13. As shown in FIG. 3, the sensing unit 10 may include a first sensor 101 and a second sensor 102. The first sensor 101 includes a first working electrode 11 with the first selective water vapour-permeable membrane 13 on its surface. For example, the surface of the first working electrode 11 is applied with one layer of membrane which allows only water molecules to permeate therethrough such that the first working electrode 11 can be in contact with water molecules in the ambient air and not in contact with the gas molecules to be measured in the ambient air, so as to generate an electrical signal caused by the change in ambient relative humidity. The first working electrode 11 may transmit the electrical signal caused by change in ambient relative humidity to the processing unit 20 so as to provide data support for acquiring the concentration of the gas to be measured. In addition, the second sensor 102 without any selective water vapour-permeable membrane can be in contact with both gas molecules to be measured and water molecules in the air. The second sensor 102 includes a second working electrode 12 which is in contact with the external environment through a sensing surface of the second sensor 102. The second working electrode 12 may generate an electrical signal which is a superimposed electrical signal caused by both gas molecules to be measured and water molecules, and transmit the superimposed electrical signal to the processing unit 20 so as to provide data support for acquiring concentration of the gas to be measured.

For example, one layer of selective water vapour-permeable membrane can be applied on the surface of the working electrode inside the electrochemical sensor by e.g., soaking the electrode into an emulsion with the Nafion material and lifting the electrode out of the emulsion. When the solvent is dried, the surface of the electrode will be naturally covered with a layer of Nafion polymer membrane. The layer of Nafion polymer membrane can have a thickness of several micrometers to several hundreds of micrometers, on a premise that, the presence of the layer does not affect the diffusivity of water molecules and the speed at which the water molecules contact the electrode, and at the same time can prevent gas molecules to be measured from permeating therethrough and contacting the electrode.

In some other embodiments of the present disclosure, the above electrode applied with the selective water vapour-permeable membrane may be incorporated together with the working electrode that does not have the selective water vapour-permeable membrane on its surface into one single sensor with a purpose to simplify the structure. The electrode is positioned inside the sensor and is in the same environment as that of the working electrode without the water vapour-permeable membrane, producing almost the same response to the change in ambient relative humidity as the working electrode without the water vapour-permeable membrane. Particularly, the sensing unit 10 according to the embodiment of the present disclosure includes one sensor that has inside both the first working electrode 11 and the second working electrode 12. Here, the first selective water vapour-permeable membrane 13 is provided on the surface of the first working electrode 11 (for example, by applying the first selective water vapour-permeable membrane 13 on the surface of the first working electrode 11 as mentioned above), or the first selective water vapour-permeable membrane 13 is provided on the sensing surface of the sensor and only covers the part through which the first working electrode 11 is in contact with the external environment. In this way, the first working electrode 11 is allowed to be only in contact with water molecules and to be not in contact with gas molecules to be measured, so as to generate a humidity electrical signal caused by change in ambient relative humidity. The second working electrode 12 is configured to be in contact with both gas molecules to be measured and water molecules to generate a superimposed electrical signal caused by both the water molecules and the gas molecules to be measured. The humidity electrical signal and the superimposed electrical signal are transmitted to the processing unit 20 so as to provide data support for acquiring concentration of the gas to be measured.

In the above embodiments, it can be equivalently seen that the first sensor 101 provided with the first selective water vapour-permeable membrane 13 at its sensing surface can be replaced with the first working electrode 11 which is coated with a selective water vapour-permeable material or the first working electrode 11 which is provided with the first selective water vapour-permeable membrane 13 at its sensing surface through which the first working electrode 11 is in contact with the ambient air. The first working electrode 11 applied with the membrane and the second working electrode 12 which is a normal working electrode can share the same reference electrode and the same auxiliary electrode in one same sensor, to further simplify the structure, that is, only one sensor is needed to perform humidity signal correction instead of two.

In the embodiments, each sensor may include at least one auxiliary electrode, one reference electrode and one counter electrode For example, each sensor may include one or two auxiliary electrodes, one or two reference electrodes and one or two counter electrodes. Any one or more of the many combinations can be adopted according to the specific needs.

For example, in a first embodiment, the sensing unit 10 may include two sensors, each of which includes one working electrode, one counter electrode and one reference electrode. Here, the sensing surface of one sensor is provided with the selective water vapour-permeable membrane 13 or the surface of the working electrode of the sensor is applied with the selective water vapour-permeable membrane. In a second embodiment, the sensing unit 10 may include two sensors, each of which includes one working electrode, one auxiliary electrode, one counter electrode and one reference electrode. Here, the sensing surface of one sensor is provided with the selective water vapour-permeable membrane 13 or the surface of the working electrode of the one sensor is applied with the selective water vapour-permeable membrane. In a third embodiment, the sensing unit 10 may include one sensor which includes two working electrodes, one auxiliary electrode, two counter electrodes and one reference electrode. Here the surface of one working electrode is covered by the selective water vapour-permeable membrane 13. In a word, the sensing unit 10 can be realized in any of the various combinations. The above only provides exemplary combinations. Other combinations are also encompassed within the scope of the structure of the sensing unit 10 of the present disclosure and are not listed for brevity purposes.

In some embodiments, for the sensing unit 10 without the auxiliary electrode, for example the sensing unit 10 as mentioned in the first embodiment, the processing unit 20 may acquire the concentration of the gas to be measured based on the following equation:

$$[P](t) = \frac{(W_2(t) - b \times A_2(t) - c)}{s}; \quad \text{equation (1).}$$

Figure 4:
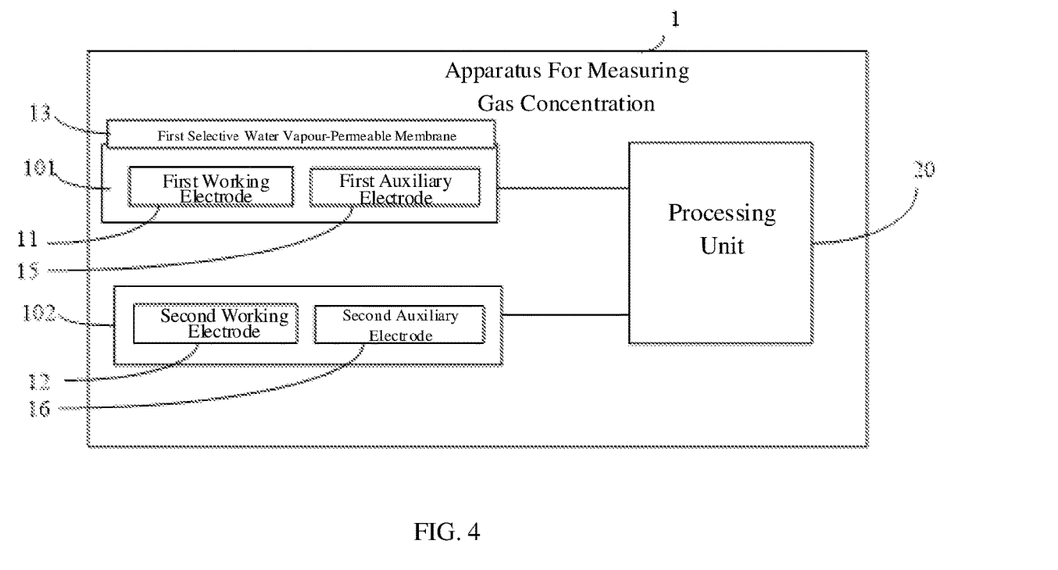
FIG. 4 is a block diagram of an apparatus for measuring gas concentration according to still yet another embodiment of the present disclosure.

Alternatively, in some embodiments, for the sensing unit 10 including the auxiliary electrode as illustrated in FIG. 4, this sensing unit 10 includes a first sensor 101 and a second sensor 102. The first sensor 101 includes a first working electrode 11, a first auxiliary electrode 15 and a first selective water vapour-permeable membrane 13. The second sensor 102 includes a second working electrode 12 and a second auxiliary electrode 16. The processing unit 20 may acquire the concentration of the gas to be measured based on the following equation:

$$[P](t) = \frac{(W_2(t) - \alpha \times W_1(t) - b \times (A_2(t) - A_1(t)) - c)}{s}; \quad \text{equation (2).}$$

In the above two equations, $[P](t)$ represents the concentration of the gas to be measured, $W_2(t)$ represents the detected electrical signal of the second working electrode, $W_1(t)$ represents the detected signal of the second auxiliary electrode, $A_2(t)$ represents the detected signal of the first working electrode, $A_1(t)$ represents the detected signal of the first auxiliary electrode, all measured at time t, and a, b, c and s are empirical coefficients which are to be determined through calibration experiments.

The above only provides two exemplary examples for calculating the concentration of the gas to be measured. In particular, the equation may be modified based on a particular environment or parameter determination purpose. These modified equations obtained based on formal transformation of the above two equations are also encompassed in the scope of the present disclosure.

Further, when using a gas sensor, one of the key steps is to determine the values of related constants such as the values of a, b, c and s in the above equations properly, and such process is usually called sensor calibration. When calibrating, the sensing unit 10 may be placed in an environment where the gas to be measured is present, which is often an outdoor environment where temperature, relative humidity and concentration of the gas to be measured change continuously with time, but can also be other environments such as a laboratorial environment in which relative humidity and temperature change in a controlled way.

Taking the sensing unit 10 shown in FIG. 4 as an example, the superimposed electrical signal generated from the second working electrode 12 is written as $W_2(t)$, the electrical signal generated from the second auxiliary electrode 16 is $W_1(t)$, both measured at time t. Correspondingly, the humidity electrical signal generated from the first working electrode 11 is written as $A_2(t)$, and the electrical signal generated from the first auxiliary electrode 15 is $A_1(t)$, both measured at time t. For the sensor sharing a common auxiliary electrode, $W_1(t)=A_1(t)$. At the same time, the concentration of the gas to be measured at time t in the environment in which the sensor is placed is written as $[P](t)$, which can either be measured by a reference instrument (including but not limited to measuring gas concentrations in the outdoor environment), or be calculated according to a standard gas concentration or for any specific gas prepared or supplied in the laboratory environment. The measurement or calculation is not limited to any of these examples. In the embodiments, a multi-variate linear regression may be performed on the above equation (2), in which a, b and c are the parameters to be determined from the fitting, which generally correspond to the temperature compensation coefficient, the relative humidity compensation coefficient and the sensor baseline compensation coefficient, respectively. Here, a and b are dimensionless, c has the same unit as that of the output voltage acquired from I-V conversion of the output current of the sensor, usually mV (millivolt). The parameter s represents a concentration response coefficient of the sensor towards the gas to be measured, which usually is expressed in the unit of mV/ppb (millivolts per part per billion, a concentration unit for gas mixture) or other units depending on the chosen output voltage unit of the sensor and the gas concentration unit specifically used.

The specific duration of the calibration process, the environment in which the calibration process is performed and the selected ranges for changes in relative humidity and temperature for the calibration process and so on can be decided by an experienced user of the sensor, and therefore will not be particularly defined here, so long as the experimental data and information acquired in the calibration period allow the respective parameters in equation (2) to be determined to a desired accuracy. Further, in the above equation (2), the concentration response coefficient s may be set as a function of temperature (meaning that the sensitivity of the sensor changes with temperature) depending on the range and rate of change of temperature and relative humidity during the calibrating process, as well as the range of gas concentration and accuracy of the gas concentration data as measured by the reference instrument. If however the experimental data does not allow for a precise determination of the temperature-dependence of s, s may be assumed as a constant and does not change as the temperature. In other words, sometimes the experimental data does not contain enough information to accurately determine the temperature-dependence of s. Similarly, a, b and c may also have some functional relations with temperature, relative humidity and atmospheric pressure, but whether or not the above functional relations can be accurately extracted depends on whether the data acquired in the calibration process contains sufficient information. Thus, in the embodiments of the present disclosure, the user can participate in the optimizing process and choose a parameterized solution with different a, b, c and s according to particular environmental characteristics.

The above equation (2) can also be further simplified, especially when the calibration data does not allow for accurate determination of the values of parameters such as a or b. Generally, manufacturers of electrochemical sensors make the sensing or the auxiliary electrodes to be as similar to each other as possible, which means that a or b can often be set as 1 without greatly deteriorating the fitting quality.

As illustrated above, the key of the calibration algorithm is the multi-variate linear regression, mainly including an approximate temperature compensation term $a \times W_1(t)$, an approximate relativity humidity compensation term $b \times (A_2(t) - A_1(t))$, and a baseline compensation term c.

After calibration, all the coefficients have known values, and the processing unit 20 can acquire the concentration of the gas to be measured by removing the temperature drift, relative humidity drift and the baseline drift according to the electrical signal of the first working electrode 11, the electrical signal of the second working electrode 12 and the detected signal of the auxiliary electrode, for example by correcting electrical signal drift due to changes in temperature and relative humidity based on the above equation (2), which can improve the accuracy of the calculation and simplify the algorithm.

Another method for determining parameters such as a, b, c and s is given in the following. In this calibration method, the first sensor 101 adhered with the selective water vapour-permeable membrane or the first working electrode 11 coated with the selective water vapour-permeable material may be still kept in the adhered or coated state, and a second selective water vapour-permeable membrane may be manually or electromechanically added onto the sensing surface of the second sensor 102 or the second working electrode 12 which were originally not sealed with the selective water vapour-permeable membrane or the selective water vapour-permeable material. This membrane may later be either manually or electromechanically removed from the second sensor 102 or the second working electrode 12. When adding the selective water vapour-permeable membrane or material, the sealing must be well guaranteed to make sure that gas molecules to be measured cannot reach the surface of the second working electrode.

The first and second sensors may be placed in an outdoor or laboratory environment where temperature and relative humidity change in a controlled way. When the second sensor 102 or the second working electrode 12 are sealed and covered by the selective water vapour-permeable membrane, $W_1(t)$, $W_2(t)$, $A_1(t)$ and others are continually recorded. The time length for recording, the environment in which the calibration is performed and the variation ranges for temperature and relative humidity can all be decided by an experienced user. After the experiment is finished, a multi-variate regression can be performed using the following equation:

$$0 = (W_2(t) - a \times W_1(t) - b \times (A_2(t) - A_1(t)) - c); \qquad \text{equation (3)}.$$

from which the values of a, b, and c can be accurately determined.

In this method, since the second sensor or the second working electrode are not in contact with the gas to be measured, the sensitivity coefficient s of the sensor or the working electrode responding to the gas to be measured cannot be determined. Here, when the sensor or the working electrode is not covered by the selective water vapour-permeable membrane, the value of s can either be accurately determined by deploying this sensor or working electrode together with a reference instrument in an outdoor environment or by exposing the sensor or the working electrode to the gas to be measured with a known concentration in a laboratory. The details thereof will not be discussed here.

A person skilled in the art may understand that the above calibration method can be realized manually or automatically in a controlled way, so as to be performed repeatedly as needed at different instances and/or at different locations where the sensor is located. Details thereof will not be discussed and are not limited to any example. In a particular implementation, one or more of the parameters a, b, c and s can be fixed selectively at the value(s) of corresponding parameters determined from calibration process in history, and the free float of other parameters are allowed. Details thereof are not to be discussed here and are not limited to any example.

Here, through operations of either the second sensor 101 or the second working electrode 12, the user may perform calibration of related parameters in the above equations for the calculation of gas concentrations conveniently at any time and any place as needed, by for example setting the second sensor 101 or the second working electrode 12 at least in the following ways.

In some embodiments, for the sensing unit 10 using one sensor, the first selective water vapour-permeable membrane 13 may be applied on the sensing surface of the sensor and cover the part of the sensing surface through which the first working electrode 11 is in contact with the external environment, and the first selective water vapour-permeable membrane 13 may selectively cover or not cover the part of the sensing surface through which the second working electrode 12 is in contact with ambient air. For example, the first selective water vapour-permeable membrane 13 may be foldable. When calibrating, the first selective water vapour-permeable membrane 13 may be unfolded and set to cover the part of the sensing surface through which the second working electrode 12 is in contact with ambient air, and constants such as a, b and c can be calibrated as mentioned in the above embodiments. When the first selective water vapour-permeable membrane 13 is folded, the first selective water vapour-permeable membrane 13 does not cover the part of the sensing surface through which the second working electrode 12 is in contact with the ambient air, and at this point, the second working electrode 12 can be in contact with the target gas to be measured and thereby measure its concentration.

In some other embodiments, similar to the configuration of the first selective water vapour-permeable membrane 13, a selective operation may be performed on the second sensor 102 or the second working electrode 12 so as to allow the second working electrode 12 to be able to either measure the gas concentration or to enter the coefficient calibration mode as needed. Particularly, the sensing unit 10 may also include a second selective water vapour-permeable membrane which has the same characteristic and function as those of the first selective water vapour-permeable membrane 13. The second selective water vapour-permeable membrane may be detachably or movably provided on the sensing surface of the second sensor 102, or the second selective water vapour-permeable membrane may be detachably or movably provided on the part of the sensing surface through which the second working electrode 12 is in contact with the external environment. For example, when calibrating the coefficients, the second selective water vapour-permeable membrane may cover the sensing surface of the second sensor 102 so as to allow the second working electrode 12 to be in contact with water molecules and prevent the second sensor 102 from being in contact with the gas molecules to be measured. At this point, the electrical signals of the first working electrode 11, the second working electrode 12 and so on can be recorded synchronously, and the values of a, b and c are determined based on the above calibrating process and equation (3). When entering the gas concentration measurement mode, the second selective water vapour-permeable membrane may be detached or removed to perform gas concentration measurement as in the above-mentioned embodiments.

As stated above, through the use of a freely movable or detachable selective water vapour-permeable membrane on the second working electrode 12 or its sensing surface, the user of the sensing unit can conveniently calibrate the empirical coefficients as needed, avoiding the need of having to seek technical support from the manufacturer or dedicated technicians.

Further, the above equation (2) allows the user to understand the temperature and relative humidity induced drifts from a first-principles perspective, and can acquire a parameterized solution with a clear physical explanation such as the temperature drift, the relative humidity drift and the baseline drift. As a result, the calibration process is easier to understand by users of the sensor and rationality of the output results is easier to evaluate.

A sensor for measuring gas concentration according to an embodiment of the present disclosure will be described with reference to the drawings in the following.

Figure 5:
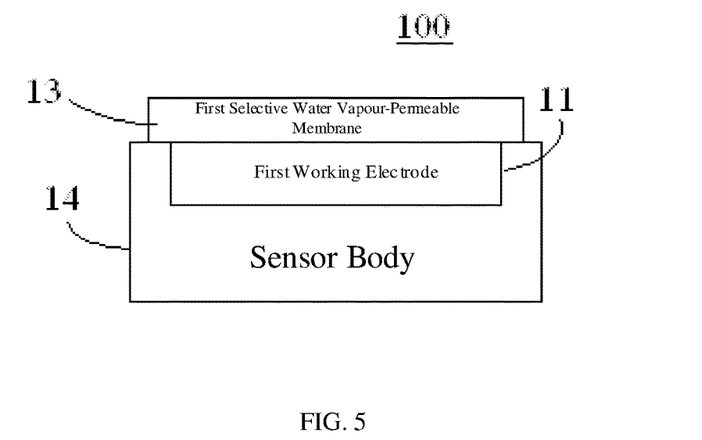
FIG. 5 is a block diagram of a sensor for measuring gas concentration according to an embodiment of the present disclosure.

FIG. 5 is a block diagram of a sensor according to one embodiment of the present disclosure. As shown in FIG. 5, the sensor 100 according to the embodiment of the present disclosure includes a sensor body 14, a first working electrode 11 and a first selective water vapour-permeable membrane 13. The first working electrode 11 is embedded inside the sensor body 14 and is in contact with the external environment through a sensing surface. The first selective water vapour-permeable membrane 13 may be applied to seal the sensing surface of the first working electrode 11 through which this electrode is in contact with ambient air. In this way, the first working electrode 11 is only allowed to be in contact with water molecules in the ambient air but not the gas molecules to be measured, so as to generate an electrical signal change characteristic that is only caused by the change in ambient relative humidity. Alternatively, the first selective water vapour-permeable membrane 13 may be provided on the surface of the first working electrode 11 (for example, the surface of the first working electrode 11 may be coated with the selective water vapour-permeable membrane) to allow the first working electrode 11 to only be in contact with water molecules but not the gas molecules to be measured, so as to generate an electrical signal change characteristic that is only caused by the change in ambient relative humidity. The sensor 100 may then be combined with a sensor without the selective water vapour-permeable membrane 13 so as to measure the concentration of the gas to be measured, realizing a high accuracy.

According to the embodiment of the present disclosure, with sensor 100 and the first selective water vapour-permeable membrane 13, electrical signal caused by the change in ambient relative humidity can be isolated, to provide data support for acquiring concentration of the gas to be measured.

Figure 6:
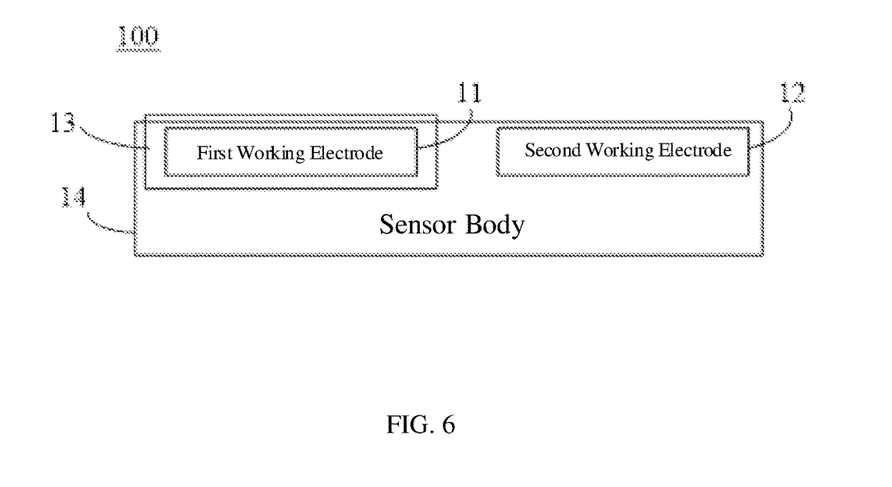
FIG. 6 is a block diagram of a sensor for measuring gas concentration according to another embodiment of the present disclosure.

In some embodiments, as illustrated in FIG. 6, the sensor 100 may further include a second working electrode 12 in the sensor body 14, and this second working electrode 12 is in contact with the external environment through a sensing surface. When measuring the gas concentration, this second working electrode 12 is in contact with both water molecules and gas molecules to be measured in the ambient air, to produce a superimposed electrical signal caused by water molecules and gas molecules to be measured. Particularly, for the sensor 100 in which the sensing surface of the first working electrode 11 is covered by the first selective water-permeable film 13 or the surface of the first sensing electrode 11 is cladded with the first selective water-permeable film 13, the concentration of the gas to be measured may be acquired based on the electrical signals generated by the first working electrode 11 and the second working electrode 12. Regarding the specific calculation process, reference may be made to the above-mentioned embodiments.

In the embodiments of the present disclosure, the sensor 100 may include one or more auxiliary electrodes and one or more reference electrodes. For example, the sensor 100 may include one or two auxiliary electrodes and one or two reference electrodes. Any one or more of the various combinations may be adopted according to particular needs and are not further discussed here.

In some embodiments, through operation of the second sensing electrode 12, the second working electrode 12 may either measure gas concentration or to perform calibration of related parameters in the calculation equation of gas concentration. For example, the second sensor 101 or the second working electrode 12 may be configured in the at least following ways.

In some embodiments, the first selective water vapour-permeable membrane 13 may be provided on the sensing surface of the sensor and cover the part through which the first working electrode 11 is in contact with the external environment. Additionally, this first selective water vapour-permeable membrane 13 may selectively cover or not cover the part of the sensing surface through which the second working electrode 12 is contact with the external environment. For example, when the first selective water vapour-permeable membrane 13 is set as not to cover the second working electrode 12, the gas concentration may be measured as in the above-mentioned embodiments. When the first selective water vapour-permeable membrane 13 is set to cover the second working electrode 12, values of a, b and c may be determined according to the above-mentioned calibrating processes by recording the electrical signals of the second sensing electrode 12.

Figure 7:
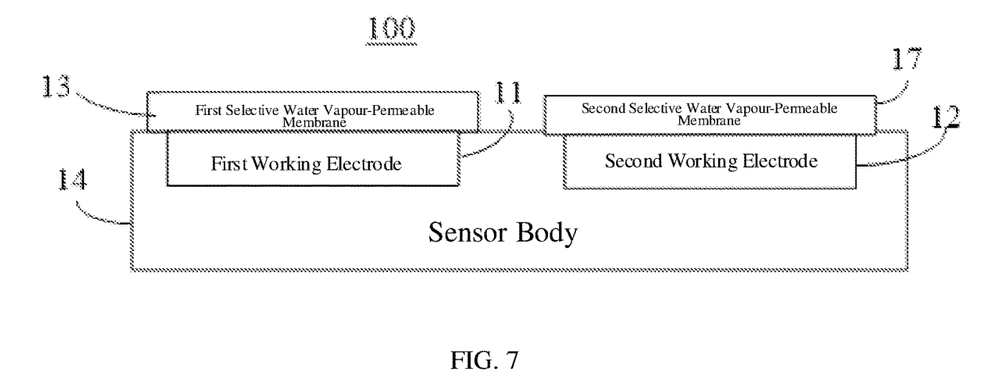
FIG. 7 is a block diagram of a sensor for measuring gas concentration according to yet another embodiment of the present disclosure.
Figure 8:
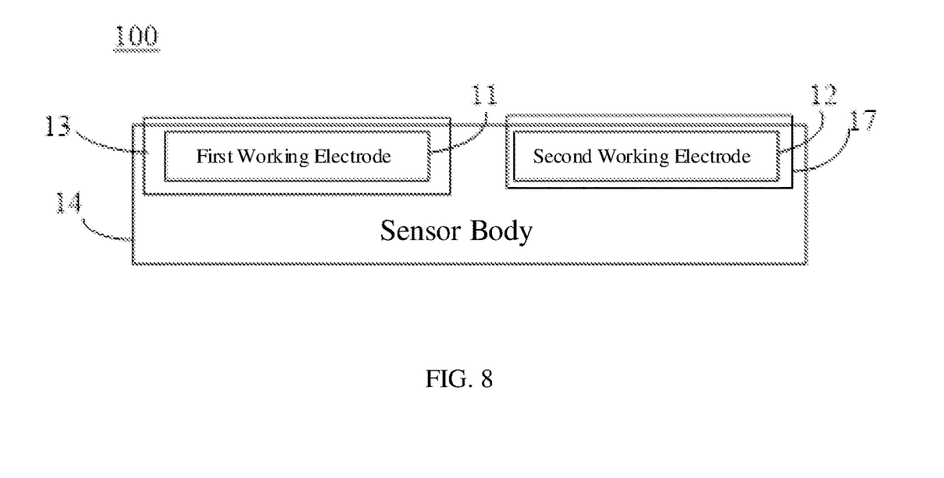
FIG. 8 is a block diagram of a sensor for measuring gas concentration according to still yet another embodiment of the present disclosure.

In some other embodiments, similar to the configuration of the first selective water vapour-permeable membrane 13, a selective operation may be performed on the second sensor 102 or the second working electrode 12 to allow the user to conveniently calibrate empirical coefficients in the calculating equation for the gas concentration. In particular, as shown in FIG. 7 or FIG. 8, the sensor 100 may further include a second selective water vapour-permeable membrane 17 that has the same characteristic and function as those of the first selective water vapour-permeable membrane 13. The second selective water vapour-permeable membrane 17 may be detachably or movably provided on the sensing surface of the second working electrode 12 which is in contact with the external environment, so as to selectively cover or not cover the part through which this second working electrode 12 is in contact with the external environment. For example, as shown in FIG. 7, the second selective water vapour-permeable membrane 17 may be provided on the sensing surface of the sensor 100 to cover the part through which the second working electrode 12 is in contact with the external environment. Alternatively, the second selective water vapour-permeable membrane 17 may be detachably or movably provided on the surface of the second working electrode 12. For example, as shown in FIG. 8, the second selective water vapour-permeable membrane is set as covering the surface of the second working electrode 12. Here, FIG. 7 and FIG. 8 only provide examples of the configuration of the first selective water vapour-permeable membrane 13 and the second selective water vapour-permeable membrane 17. These two membranes may be configured in other forms and are not limited to any of the above-mentioned examples.

For example, when calibrating the coefficients, the second selective water vapour-permeable membrane 17 may be set as adhering to the sensing surface of the second sensor 102 and covering the part through which the second working electrode 12 is in contact with the external environment, such that the second working electrode 12 may be in contact with water molecules and not in contact with gas molecules to be measured. Values of a, b and c may be determined according to the above-mentioned calibration process by recording the response signals to relative humidity and temperature and baseline signals of the second working electrode 12. Alternatively, when measuring gas concentration, the gas concentration is measured as in the above-mentioned embodiments by removing the second selective water vapour-permeable membrane 17.

As above, for the second working electrode 12, by adopting a freely movable or detachable configuration for the selective water vapour-permeable membrane, calibration of the empirical coefficients may be performed repeatedly and conveniently as needed, without the trouble of having to seek technical support from the manufacturer or a dedicated technician, time-saving and convenient.

Figure 9:
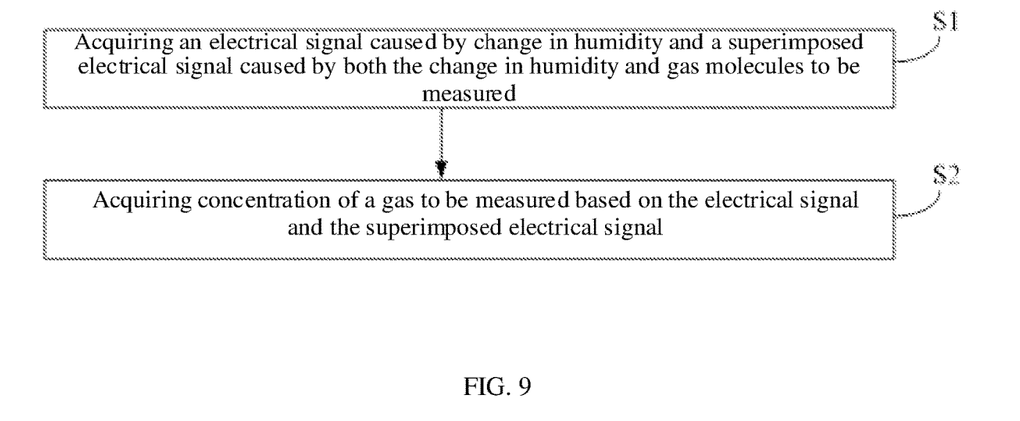
FIG. 9 is a flowchart of a method for measuring gas concentration according to an embodiment of the present disclosure.

Based on the apparatus and sensor described in the aforementioned embodiments, an embodiment of the present disclosure further provides a method for measuring gas concentration. FIG. 9 is a flowchart illustrating the method for measuring gas concentration according to one embodiment of the present disclosure. As shown in FIG. 9, the method includes at least step S1 and step S2.

At Step S1, an electrical signal caused by the change in ambient relative humidity is acquired, and a superimposed electrical signal caused by both the change in ambient relative humidity and gas molecules to be measured is also acquired.

Here, for a configuration of the sensing unit and a configuration of each of the electrodes, reference may be made to the description of the above-mentioned embodiments.

At Step S2, concentration of the gas to be measured is acquired based on the electrical signal caused by the change in ambient relative humidity and the superimposed electrical signal.

Particularly, the concentration of the gas to be measured may be acquired according to the above-given equation (1). Here, regarding the calibration process for the respective parameters, reference may be made to the description in the above-mentioned embodiments.

Alternatively, for the sensing unit including auxiliary electrodes, the concentration of the gas to be measured may be acquired according to the above-given equation (2). Here, the detected signal from the second auxiliary electrode can be considered as a temperature-related term, the humidity electrical signal and the detected signal of the first auxiliary electrode may be considered as a relative humidity-related term, and the processing unit may acquire the electrical signal related to the gas molecules to be measured by subtracting both the temperature-related term and the relative humidity-related term from the superimposed electrical signal caused by both water molecules and gas molecules to be measured, so as to determine the concentration of the gas to be measured.

In the method for measuring gas concentration according to the embodiments of the present disclosure, based on the selective water vapour-permeable membrane, the first sensing electrode and the second sensing electrode, the humidity electrical signal caused by water molecules is isolated, and the electrical signal related to gas molecules to be measured is acquired by subtracting the temperature-related term and the relative humidity-related term from the superimposed electrical signal caused by both water molecules and gas molecules to be measured. The method can quickly and effectively correct for ambient relative humidity and temperature effects and can accurately determine the concentration of the gas to be measured in ambient air, and therefore has a wide applicability.

It shall be noted that, any sensor that is responsive to changes in temperature and relative humidity, such as an electrochemical sensor or other sensor having the equivalent function, may be adopted to accurately measure a humidity response signal of the sensor by providing a selective vapour-permeable membrane on the surface of the sensor or cladding or coating the surface of the sensing material with a selective vapour-permeable membrane as in the inventive idea given above, and correct for the baseline drift of the sensor caused by the relative humidity through further mathematical analysis and baseline subtraction, etc.

In the present disclosure, the description with reference to the terms "one embodiment", "some embodiments", "an exemplary embodiment", "an example", "a specific example", or "some examples", etc., means that specific features, structures, materials, or characteristics described in conjunction with the embodiment(s) or example(s) are included in at least one embodiment or example of the present disclosure. In the present disclosure, any illustrative reference of the above terms does not necessarily refer to the same embodiment(s) or example(s).

Although the embodiments of the present disclosure have been shown and described above, it can be appreciated by those of ordinary skill in the art that various changes, modifications, replacements and variants can be made to the above embodiments without departing from the principle and spirit of the present disclosure. The scope of the present disclosure is defined by the attached claims and equivalents thereof.

What is claimed is:

1. An apparatus for measuring gas concentration, comprising:
a sensing device comprising a first selective water vapour-permeable membrane, a first working electrode and a second working electrode, wherein the first selective water vapour-permeable membrane is configured to allow the first working electrode to be in contact with water molecules but to prevent the first working electrode from being in contact with the gas molecules to be measured, the first working electrode is configured to generate an electrical signal that is caused by change in ambient relative humidity, and the second working electrode is configured to generate a superimposed electrical signal caused by both the change in ambient relative humidity and reaction of the gas molecules to be measured;

wherein the sensing device comprises a first sensor and a second sensor, the first sensor comprises the first working electrode, and the second sensor comprises the second working electrode, the first working electrode is in contact with an external environment through the sensing surface of the first sensor, and the second working electrode is in contact with the external environment through the sensing surface of the second sensor, wherein the first selective water vapour-permeable membrane is provided on the sensing surface of the first sensor or on the surface of the first working electrode; or the sensing device comprises one sensor comprising the first working electrode and the second working electrode, the first working electrode and the second working electrode are in contact with the external environment through the sensing surface of the sensor, wherein the first selective water vapour-permeable membrane is provided on the surface of the first working electrode or the part of the sensing surface through which the first working electrode is in contact with the external environment;

wherein the first selective water vapour-permeable membrane is foldable in such a manner that, the first selective water vapour-permeable membrane when unfolded, covers the part of the sensing surface of said one sensor through which the second working electrode is in contact with the ambient air, and the first selective water vapour-permeable membrane when folded, does not cover the part of the sensing surface of said one sensor through which the second working electrode is in contact with the ambient air; and a processor configured to acquire concentration of the gas to be measured based on the electrical signal caused by the change in ambient relative humidity and the superimposed electrical signal.

2. The apparatus for measuring gas concentration of claim 1, wherein the first selective water vapour-permeable membrane is provided on the sensing surface of said one sensor and is configured to selectively cover the part of the sensing surface through which the second working electrode is in contact with the external environment; or the sensing device further comprises a second selective water vapour-permeable membrane, the second selective water vapour-permeable membrane is detachably or movably provided on the part of the sensing surface through which the second working electrode of said one sensor is in contact with the external environment, to selectively cover the part of the sensing surface of the said one sensor; or the sensing device further comprises a second selective water vapour-permeable membrane, the second selective water vapour-permeable membrane is detachably or movably provided on the surface of the second working electrode.

3. The apparatus for measuring gas concentration of claim 1, wherein each of the first and second sensors further comprises at least one auxiliary electrode.

4. The apparatus for measuring gas concentration of claim 1, wherein the processor is configured to acquire the concentration of the gas to be measured through the following equation:

$$[P](t) = \frac{(W_2(t) - b \times A_2(t) - c)}{s};$$

or the first sensor comprises a first auxiliary electrode, the second sensor comprises a second auxiliary electrode, and the processor is configured to acquire the concentration of the gas to be measured through the following equation:

$$[P](t) = \frac{(W_2(t) - \alpha \times W_1(t) - b \times (A_2(t) - A_1(t)) - c)}{s};$$

in which, $[P](t)$ represents the concentration of the gas to be measured, $W_2(t)$ represents a detected signal of the second working electrode, $W_1(t)$ represents a detected signal of the second auxiliary electrode, $A_2(t)$ represents a detected signal of the first working electrode, $A_1(t)$ represents a detected signal of the first auxiliary electrode, t represents time, and each of a, b, c and s represents an empirical coefficient to be calibrated.

5. The apparatus for measuring gas concentration of claim 1, wherein each of the first and second sensors comprises one or two auxiliary electrodes, one or two reference electrodes and one or two counter electrodes; or each of the first and second sensors comprises one working electrode, one auxiliary electrode, one counter electrode and one reference electrode; or said one sensor comprises two working electrodes, one auxiliary electrode, two counter electrodes and one reference electrode.

6. A method for measuring gas concentration, applied to the apparatus for measuring gas concentration of claim 1, wherein the method comprises:

acquiring an electrical signal caused by change in ambient relative humidity and a superimposed electrical signal caused by both the change in ambient relative humidity and the reaction of the gas molecules to be measured on the surface of the second working electrode; and acquiring concentration of the gas to be measured based on the electrical signal and the superimposed electrical signal.

7. The method for measuring gas concentration of claim 6, wherein the sensing device comprises the first sensor and the second sensor, the first sensor comprises the first working electrode, and the second sensor comprises the second working electrode, the first working electrode is in contact with an external environment through the sensing surface of the first sensor, and the second working electrode is in contact with the external environment through the sensing surface of the second sensor, wherein the first selective water vapour-permeable membrane is provided on the sensing surface of the first sensor or on the surface of the first working electrode, wherein the first sensor comprises a first auxiliary electrode, the second sensor comprises a second auxiliary electrode, the concentration of the gas to be measured is acquired based on the following equation:

$$[P](t) = \frac{(W_2(t) - b \times A_2(t) - c)}{s};$$

or the concentration of the gas to be measured is acquired based on the following equation:

$$[P](t) = \frac{(W_2(t) - \alpha \times W_1(t) - b \times (A_2(t) - A_1(t)) - c)}{s};$$

in which, [P](t) represents the concentration of the gas to be measured, $W_2(t)$ represents a detected signal of the second working electrode, $W_1(t)$ represents a detected signal of the second auxiliary electrode, $A_2(t)$ represents a detected signal of the first working electrode, $A_1(t)$ represents a detected signal of the first auxiliary electrode, t represents time, and each of a, b, c and s represents an empirical coefficient to be calibrated.

8. A sensor for measuring gas concentration, comprising:
a sensor body; and
a first working electrode within the sensor body, which is in contact with an external environment through a sensing surface; and
a first selective water vapour-permeable membrane, which is applied on the sensing surface of the first working electrode and completely covers the sensing surface, to allow the first working electrode to only be in contact with water molecules in the ambient air whilst prevents the first working electrode from being in contact with gas molecules to be measured, to generate an electrical signal whose change is largely caused by change in ambient relative humidity; or
the first selective water vapour-permeable membrane is applied on the surface of the first working electrode, to allow the first working electrode to only be in contact with water molecules in the ambient air and prevent the first working electrode from being in contact with the gas molecules to be measured, to generate an electrical signal whose change is largely caused by the change in ambient relative humidity;

wherein the sensor further comprises a second working electrode inside the sensor body, the second working electrode is in contact with the external environment through the sensing surface;

wherein the first selective water vapour-permeable membrane is foldable in such a manner that, the first selective water vapour-permeable membrane when unfolded, covers the part of the sensing surface of said sensor through which the second working electrode is in contact with the ambient air, and the first selective water vapour-permeable membrane when folded, does not cover the part of the sensing surface of said sensor through which the second working electrode is in contact with the ambient air.

9. The sensor for measuring gas concentration of claim 8, wherein
the first selective water vapour-permeable membrane is applied on the sensing surface and selectively cover or not cover the part of the sensing surface through which the second working electrode is in contact with the external environment; or
the sensor further comprises a second selective water vapour-permeable membrane, the second selective water vapour-permeable membrane is detachably or movably provided on the sensing surface through which the second working electrode is in contact with the external environment, to selectively cover or not cover the sensing surface; or
the sensor further comprises a second selective water vapour-permeable membrane which is detachably or movably provided on the surface of the second working electrode.

10. The sensor for measuring gas concentration of claim 8, wherein the sensor further comprises at least one auxiliary electrode.

* * * * *